United States Patent [19]

English

[11] 4,004,300
[45] Jan. 25, 1977

[54] FEMORAL PROSTHESIS

[76] Inventor: Thomas Anthony English, Westwood Close, Beverley, North Humberside, England

[22] Filed: Oct. 9, 1975

[21] Appl. No.: 621,063

[30] Foreign Application Priority Data

Oct. 14, 1974 United Kingdom ............ 44359/74

[52] U.S. Cl. .......................... 3/1.913; 128/92 CA
[51] Int. Cl.² ......................................... A61F 1/24
[58] Field of Search ........................... 3/1.9–1.913, 3/1; 128/92 C, 92 CA

[56] References Cited
UNITED STATES PATENTS 3,848,272  11/1974  Noiles ................................ 3/1.913
3,863,273  2/1975  Averill ................................ 3/1.91
3,889,299  6/1975  Osborne et al. ........................ 3/1

FOREIGN PATENTS OR APPLICATIONS 1,362,187  7/1974  United Kingdom ................. 3/1.91

Primary Examiner—Ronald L. Frinks
Attorney, Agent, or Firm—Bacon & Thomas

[57] ABSTRACT

A femoral prosthesis comprising a shank, a neck integral with the shank, and a detachable ball head supported on the neck and interchangeable with other ball heads of different external size whereby a common shank and neck can support a ball head of desired external size.

10 Claims, 3 Drawing Figures

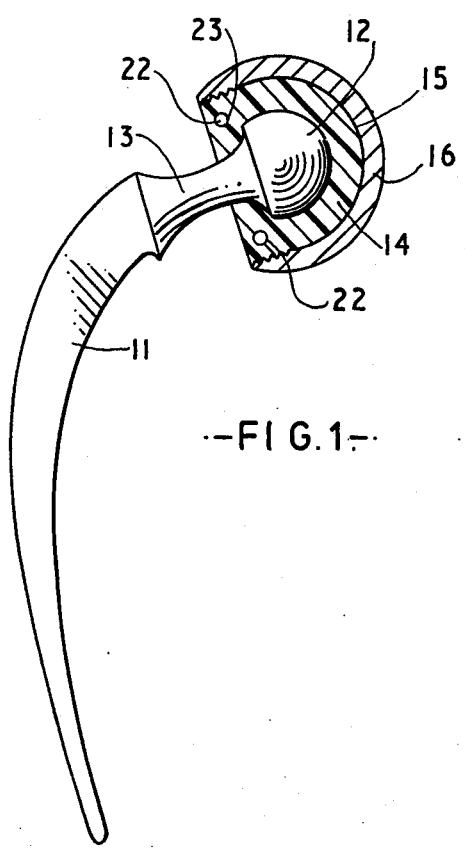
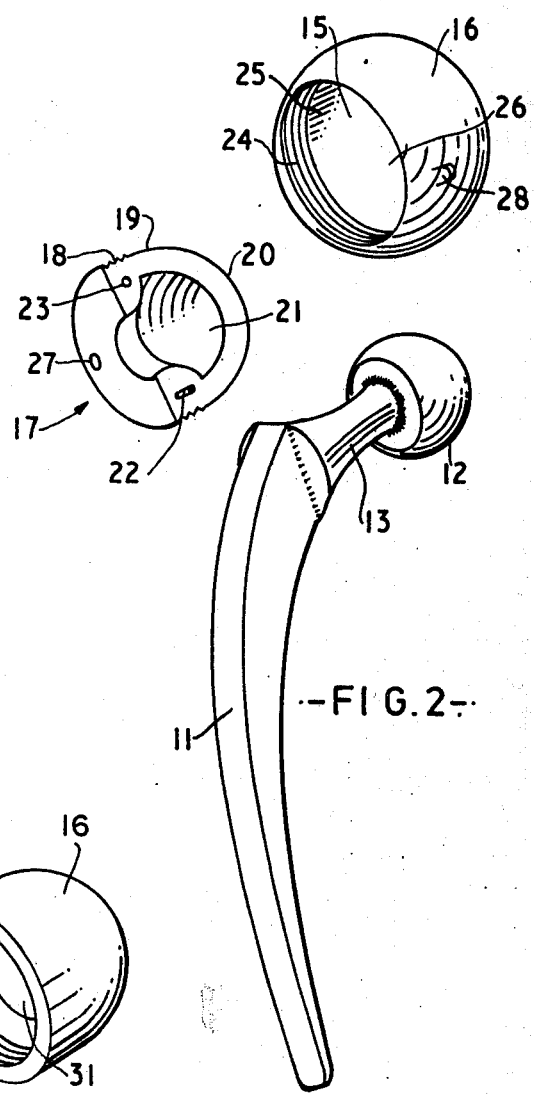
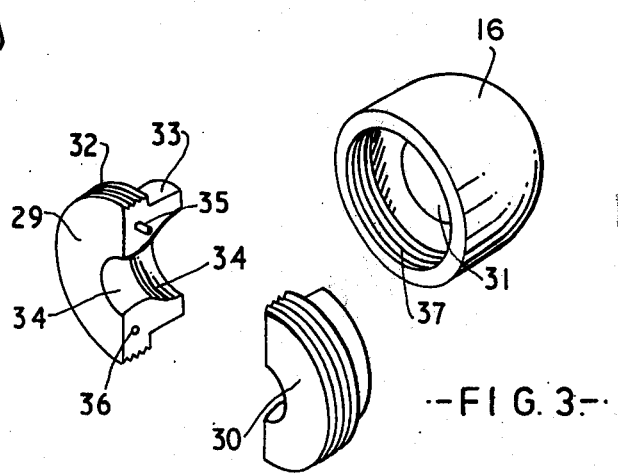

FEMORAL PROSTHESIS

The present invention relates to a prosthesis for use in bone surgery and more particularly to a prosthesis for replacement of a hip joint.

It is well known in the art to replace a diseased, or otherwise damaged, upper femur with a prosthesis comprising shank with an integral ball head. The femur is severed just below the neck to allow the natural neck and ball head to be removed, the sound bone is reamed and the shank of the prosthesis is inserted into the reamed end of the sound bone and cemented, or otherwise secured, thereto.

When the natural socket in the pelvis is healthy the ball head of the prosthesis can be engaged directly therein but, as most adults vary in size, a range of prosthesis, with differently sized ball heads must be made available during the operation to allow the surgeon to select the best ball head size for the natural socket exposed during the operation.

It has been observed that after a long period of time, and particularly with an active patient, a femoral prosthesis can cause damage to the natural socket and can in fact break down the natural socket and enter into the pelvis. In such circumstances it is essential that the natural ball socket be replaced by a socket prosthesis but this also means that the femoral prosthesis, having the natural ball size, must also be removed and replaced with a prosthesis having a small head capable of being snugly received in the ball socket prosthesis. The replacement of both parts of the ball joint can constitute a serious operation and, as the majority of patients requiring replacement of both parts after a prolonged period with one prosthesis will be at an advanced age the operation becomes increasingly serious.

The present invention seeks to provide a prosthesis for replacing the upper part of the femur and which can be adapted for receipt in any one of a plurality of natural ball sizes and further is capable of being adapted for receipt in a ball joint prosthesis.

According to the present invention there is provided a femoral prosthesis comprising a shank, a neck integral with the shank, and a ball head detachably supported by said neck.

Preferably the neck has a ball head integral therewith, said detachable ball head is supported on said integral ball head, and conveniently said detachable ball head includes a recess therein in which the integral ball head is located.

Preferably the prosthesis includes a liner, conveniently made from a plastics material, inside the detachable ball head and the liner supports the detachable ball head in spaced relationship to the other parts of the prosthesis.

Preferably the liner comprises a plurality of separable parts which, when assembled, define an external screw thread engageable with an internal screw thread in the detachable ball head and by which the liner is detachably secured in the detachable ball head.

In a preferred embodiment in accordance with the invention the detachable ball head includes a recess with an internal screw threaded portion and the liner comprises a plurality of separable parts which, when assembled, closely surround the internal ball head and part of the neck adjacent thereto, and fits snugly into the recess. The liner presents an external screw thread portion engageable with the internal screw threaded portion of the recess whereby the liner is securably detachable.

The liner may conveniently comprise two substantially identical, but diametrically opposite, half shells and locking means, such as pins and holes, may be provided for locking the two half shells to form a body of revolution. When assembled the two half shells present an external screw thread engageable with a screw thread in the recess in the detachable ball head and, when threadedly engaged and secured in the recess, the assembled half shells snugly fill said recess. The mating faces of the half shells are recessed to define, when the half shells are assembled, a cavity which snugly receives the integral ball head and part of the neck adjacent thereto.

To assemble the prosthesis the two half shells are placed one on each side of the integral ball head so that the integral ball head and the part of the neck adjacent thereto seats snugly in the cavity defined by the recesses in the mating surfaces of the half shells. The detachable ball head is then placed over the liner and rotated to threadedly engage the externally threaded portion of the assembled half shells. The detachable ball head is thus screwed on to the liner and the exposed end face of the liner conveniently includes recesses, engageable by a suitable spanner, and the detachable ball head may also include recesses, engageable by a suitable spanner, for locking the liner in threaded engagement with the detachable ball head.

To remove the detachable ball head it is only necessary to apply the appropriate spanners and unscrew the detachable ball head, split the half shells, and the integral ball head is exposed.

It will be appreciated that with the above arrangement each and every femoral prosthesis to be used can have an internal ball head of a standard diameter, the liner can be of standard size, and a plurality of detachable ball heads of uniform recess size, but different external diameters, can be provided to fit any desired size of natural socket.

In an alternative arrangement the liner comprises a hemispherical part which seats in the base of the recess and said liner part presents a hemispherical recess for receiving that half of the integral ball head remote from the neck. The liner further includes two substantial identical, but diametrically opposite, half shells, recessed in their mating faces to receive that half of the integral ball head adjacent the neck and part of the neck adjacent to ball head, and which, when assembled, presents an external screw thread engageable in the screw thread in the recess of the detachable ball head.

In a still further embodiment the base of the recess in the detachable ball head is hemispherical and the liner includes a hemispherical portion which seats in the hemispherical base of the ball head. Said hemispherical liner portion present a hemispherical recess for receiving that half of the integral ball head remote from the neck. The liner further includes a split ring, resiliently deformable, and which, when passed around the neck of the prosthesis, enters loosely into the recess in the detachable ball head and presents an arcuate section which snugly engages that half of the integral ball head adjacent the neck. The liner also includes an annular sleeve, externally screw cut to engage in the screw thread in the detachable ball head, and said sleeve surrounds the split ring and presents a radial abutment surface, which engages with the split ring to locate said split ring axially of the recess when the liner is assembled.

The sleeve, and the adjacent exposed surface of the ball head, may, as previously described, include means engageable by suitable hand tools for tightening and loosening the threaded sleeve in the detachable ball head.

It will be seen that with all the above described preferred embodiments the detachable ball head is retained with the liner by a screw thread, such securement means offering ready assembly and interchanging of different ball head presentations for the prosthesis and, when assembled, offering a secure retention of the assembly.

In a still further alternative embodiment the liner comprises three separable parts, two of which are substantially identical half shells recessed to receive the integral ball head therein when the two shell halves are assembled, and the third part having an external screw thread thereon. The third part is engageable with the shank side of the assembled shells and capable of abutting the two half shells when the half shells are assembled about the integral ball head. A detachable ball head, having a recess therein to receive the liner, is passed over the two half shells and threadedly engaged with the screw thread on the third part of the liner.

Preferably the integral ball head is of a size capable of being received in the ball socket of a conventional ball socket prosthesis so that without the liner and detachable ball head the prosthesis can be used in the normal manner when both the upper part of the femur and the natural ball socket are to be replaced. On the other hand, with the liner and one of a plurality of different sizes of detachable ball heads, the prosthesis can be used for engagement with a natural ball socket when only the upper part of the femur is to be replaced.

Thus, the prosthesis in accordance with the invention can be used in an operation to replace only the upper part of the femur and if, after a period of time, it is found necessary to replace the natural ball socket the surgeon has only to replace the natural ball socket with a ball socket prosthesis and detach the detachable ball head and the liner from the prosthesis in the upper part of the femur to expose the integral ball head and thus the femur prosthesis need not be disturbed with a result that the operation is simplified.

The invention will now be described further by way of example with reference to the accompanying drawings in which;

FIG. 1 shows a side view of a prosthesis with a detachable ball head and liner shown in cross-section on the centre line of the prosthesis, FIG. 2 shows an exploded perspective view of the prosthesis and detachable ball head assembly illustrated in FIG. 1 with one of the shells removed for clarity, and FIG. 3 shows an exploded perspective view of an alternative liner construction and detachable ball head.

The prosthesis shown in FIGS. 1 and 2 comprises a shank 11, adapted to be driven into the upper part of the femur when the damaged femur head has been removed, and integral ball head 12, and a neck 13, of smaller cross-section than the head 12, connecting the head 12 to the shank 11. The ball head 12, is dimensioned to be received in a conventional ball socket prosthesis.

A liner, generally indicated by reference numeral 14, made from a plastics material, surrounds the ball head 12, and is received in a recess 15 in a detachable ball head 16.

The liner 14 is, as illustrated in FIG. 2, formed by two identical half shells 17, only one of which is shown in FIG. 2, which, when assembled, define an annular portion 18, externally threaded, with a reduced cylindrical portion 19 blending into a hemispherical end 20. The liner halves 17 are recessed, as shown by numeral 21, so that, when the halves 17 are assembled, the recesses 21 define a cavity for closely receiving the ball head 12 and part of the neck 13 of the prosthesis therein.

The two shell halves 17 are located in axial alignment by pins 22 which engage in co-operating blind bores 23 in the shell halves 17.

The detachable ball head 16 for co-operating with the liner 14 illustrated in FIG. 2 has its recess comprising a screw-cut cylindrical bore part 24 with a reduced plain cylindrical bore portion 25 extending therefrom and blending into a hemispherical recess 26.

To assemble the liner 14 and detachable head 16 illustrated in FIG. 2 with a prosthesis 11,12,13 the two shell halves 17 are placed one on each side of the head 12, pins 22 are located in the bores 23 in each shell half 17, and the shell halves 17, are closed tightly about the head 12. The ball head 16 is then axially displaced over the hemispherical portion 20 of the liner, over the reduced cylindrical portion 19 and then rotated to engage its thread 24 onto the thread on the annular portion 18 of the liner. Once the head 16 is tightly screwed onto the liner 14 said liner 14 fills the recess 15 and a rigid construction is obtained thereby.

Recesses 27 in the liner and recesses 28 in ball head 16 allow the two parts to be engaged by suitable spanners for tightening and releasing the assembly.

The arrangement illustrated in FIG. 3 is similar to that shown in FIG. 2, but differs in that the liner comprises two shell halves 29 and 30 with a hemispherical part 31. The two shell halves are identical and, when assembled, define an annular threaded portion 32, reduced cylindrical portion 33, and a cavity 34 which receives part of the neck 13 and that part of the ball head 12 on the neck side of maximum diameter of ball head 12.

The two shell halves 29 and 30 are located by pins 35 engaged in bores 36 in said halves.

The hemispherical part 31 illustrated in its operative position within the detachable ball head 16, has a hemispherical recess therein which co-operates with the cavities 34 in the shell halves to encase the integral ball head 12.

The detachable ball head 16 is recessed to receive the liner 29, 30, 31 snugly, thereinto and is screw cut at 37 to engage with the threaded portion 32 on the liner.

It will be seen that with the arrangement illustrated in FIGS. 1 and 2 a surgeon can replace a damaged upper femur with a prosthesis and the detachable ball head 16 can be selected from a range of sizes to suit the patient. With a healthy natural ball joint the prosthesis can give long and useful service but, in the event that the prosthesis damages the natural ball joint, the surgeon need only replace the natural ball joint socket with a prosthesis, unscrew the detachable ball head 15 from the femur prosthesis and remove the liner to expose the ball head 12 without disturbing the union between the prosthesis 11,12,13 and the femur. Once the ball head 12 has been exposed the prosthesis 11,12 and 13 is of a size to cooperate with the ball joint prosthesis.

Thus, by avoiding the need to replace the femur prosthesis, the operation is simplified, the operation time can be reduced, and a more rapid recovery of the patient obtained.

I claim:

1. A femoral prosthesis of the type having a shank, a neck extending from the shank and fixed ball head carried by the neck, which prosthesis comprises, in combination:
   a. a split detachable liner for completely enclosing and conforming to the shape of the fixed ball head and a portion of the neck adjacent thereto, which liner includes a first screw thread on a portion of its outer surface; and
   b. a detachable ball head having a recess corresponding substantially to the outer configuration of the liner, which recess includes a second screw thread corresponding to the first screw thread such that the liner may be snugly fitted and secured within the recess by engaging the first and second screw threads.

2. The femoral prosthesis of claim 1 wherein the split liner includes two substantially identical half sections.

3. The femoral prosthesis of claim 2 wherein the half sections include alignment means for facilitating the assembly of the liner.

4. The femoral prosthesis of claim 3 wherein the alignment means includes at least one pin carried by one half section and a corresponding pin bore hole formed in the other half section.

5. The femoral prosthesis of claim 1 wherein the liner is of plastic material.

6. The femoral prosthesis of claim 1 wherein the recess in the detachable ball head includes a substantially hemispherical portion for mating with a corresponding hemispherical portion on the liner.

7. The femoral prosthesis of claim 1 wherein the liner includes an abutment surface for retaining the liner in the detachable ball head.

8. The femoral prosthesis of claim 1 wherein the liner includes:
   a. a substantially hemispherical portion for seating against the bottom of the recess in the detachable ball head; and
   b. two substantially identical half sections having the first screw thread formed on their outer surfaces.

9. The femoral prosthesis of claim 1 further including means for cooperating with spanners to thereby facilitate the engagement and disengagement of the first and second screw threads.

10. The femoral prosthesis of claim 9 wherein said means includes recesses formed in the liner and outer surface of the detachable ball head.

* * * * *